(12) United States Patent
Wiessler et al.

(10) Patent No.: US 6,417,339 B1
(45) Date of Patent: Jul. 9, 2002

(54) DENDRIMERS BASED ON SACCHARIDES

(75) Inventors: Manfred Wiessler, Heidelberg; Markus Gschrey, Heppenheim; Willi Von der Lieth; Walter Mier, both of Heidelberg, all of (DE)

(73) Assignee: Deutsches Krebsforschungzentrum Stiftung des Offentlichen Rechts, Heidelberg (DE)

( * ) Notice: Subject to any disclaimer, the term of this patent is extended or adjusted under 35 U.S.C. 154(b) by 0 days.

(21) Appl. No.: 09/202,843

(22) PCT Filed: Jun. 18, 1997

(86) PCT No.: PCT/DE97/01278
§ 371 (c)(1),
(2), (4) Date: Mar. 8, 1999

(87) PCT Pub. No.: WO97/48711
PCT Pub. Date: Dec. 24, 1997

(30) Foreign Application Priority Data

Jun. 20, 1996 (DE) .......................................... 196 24 705

(51) Int. Cl.[7] ................................................ C08B 5/04
(52) U.S. Cl. ..................... 536/4.1; 536/17.2; 536/17.9; 536/18.5; 514/24; 514/25
(58) Field of Search ................................ 536/4.1, 17.2, 536/17.9, 18.5; 514/24, 25

(56) References Cited

U.S. PATENT DOCUMENTS

| 4,410,688 A | 10/1983 | Denkewalter et al. | 528/328 |
| 6,008,203 A | * 12/1999 | Magnani et al. | 514/61 |

FOREIGN PATENT DOCUMENTS

| EP | 0601 417 A2 | 6/1994 |
| EP | 0 649 854 A1 | 4/1995 |
| WO | WO 95/05182 | 2/1995 |
| WO | WO 95/25763 | 9/1995 |

OTHER PUBLICATIONS

D.R. Bundle, et al., *Carbohydrate Chemistry*, Ed. J. Thiem, 1990.
Chem. Absracts, vol. 125, No. 26, 1996, No. 125:329642b.
Patent Abstracts of Japan, C–1025, Feb. 10, 1993, vol. 17, No. 67, JP 4–273889 A, Sep. 30, 1992.
Patent Abstracts of Japan, C–1190, Apr. 13, 1994, vol. 18, No. 209, JP 6–9675, Jan. 18, 1994.
Aoi, K., et al., Globular Carbohydrate Macromolecule Sugar Balls . 1. Synthesis of Novel Sugar–Persubstituted Poly(amido amine) Dendrimers, Macromolecule 28:5391–5393 (1995).
Ashton, P.R., A Convergent Synthesis of a Carbohydrate-Containing Dendrimer, Angew. Chem. Int. Ed. Eng. 36(7):732–735 (1997).
Ashton, P.R., A Convergent Synthesis of CarbohydrateContaining Dendrimers, Chem Eur. J. 2(2):1115–1128 (1996).
Ballou, C.E., The Absolute Configuration of the myo–Inositol 1– Phosphates and Confirmation of the Bornesitol Configurations[1], J. Am. Chem. Soc. 82:3333–3335 (1960).
Lindhorst, T.K., Glycocoating of Oligovalent Amines: Synthesis of Thiourea–Bridged Cluster Glycosides from Glycosyl Isothiocyanates, Angew. Chem. Int. Ed. 35(17): 1953–1956 (1996).
Menzler, S., Beta–Galactosidase Catalysed Synthesis of Branched Oligosaccharide Analogues, Biotechnology Letters 11(2):269–272 (1997).
Roy, R., Glycodendrimers: A New Class of Biopolymers, Polymer News 21:226–232 (1996).
Roy, R., Synthesis of Hyper–Branched Dendritic Lactosides, Tetrahedron Letters 36(25):4377–4380 (1995).
Roy, R., Solid–Phase Synthesis of Dendritic Sialoside Inhibitors of Influenza A Virus Haemagglutinin, J. Chem. Soc. 1869–1872 (1993).
Toyokuni, T., Synthetic Carbohydrate Vaccines Based on Tumour–Associated Antigens, Chem. Soc. Rev. 231–242 (1995).
Zanini, D., Syntheses and Biological Properties of Glyco-Dendrimers, Plym Mater. Sci. Eng. 73:82–83 (1995).
Zanini, D., Synthesis of novel Dendritic Glycosides, Tetrahedron Letters 36(41):7383–7386 (1995).
Zanini, D., Novel Dendritic α–Sialosides: Synthesis of Glycodendrimers Based on a 3,3–Iminobis(propylamine) Core, J. Org. Chem. 61:7348–7354 (1996).
Zanini, D., Chemoenzymatic Synthesis and Lectin Binding Properties of Dendritic N–Acetyllactosamine, Bioconjugate Chem. 8:187–192 (1997).

* cited by examiner

*Primary Examiner*—Kathleen K. Fonda
(74) *Attorney, Agent, or Firm*—Albert P. Halluin; Vilao T. Kung; Howrey, Simon, Arnold & White, LLP

(57) ABSTRACT

The invention relates to dendrimers comprising an initiator core with at least two functional groups and at least two saccharides, a process for preparing sch dendrimers as well as uses thereof.

19 Claims, 6 Drawing Sheets

R = protecting group

R = protecting group

DENDRIMERS BASED ON SACCHARIDES

This application is the U.S. national stage entry under 35 U.S.C. 371 of PCT/DE97/01278, filed Jun. 18, 1997.

FIELD OF THE INVENTION

The present invention relates to dendrimers based on saccharides, a process for the preparation of the same as well as use thereof.

BACKGROUND OF THE INVENTION

When organic compounds are synthesized, the products are often obtained as mixtures such as racemic mixtures, i.e., as mixtures of enantiomers. Enantiomers may differ only little regarding physical properties but differ substantially with respect to their physiological effects. Thus, one enantiomer may be toxic whereas the other enantiomer may have a therapeutic effect. Therefore, the separation of enantiomers is desirable. Many attempts have been made to achieve this goal. However, the prevailing results are not satisfactory.

It is an object of the present invention to provide a product by which mixtures of products, particularly racemates, can be separated effectively.

According to the invention, this is achieved by the subject matter defined in the claims.

SUMMARY OF THE INVENTION

The present invention relates to a dendrimer comprising an initiator core having at least two functional groups and at least two saccharides.

Dendrimers are three-dimensional, highly ordered oligomeric compounds and polymeric compounds, respectively, which form on the basis of an initiator core that has several reactive groups. Substances are attached to these groups. Dendrimers of the first generation are obtained in this way. It is possible to bind to the substances of the first-generation dendrimers further substances and/or further initiator cores that can then be linked with further substances. In this connection, dendrimers of the second generation are obtained. Dendrimers of higher generations are obtained when this reaction sequence is repeated.

The term "initiator core having at least two functional groups" relates to cyclic compounds having at least two functional groups, e.g., hydroxy groups, amino groups, carboxylic acid groups, metallo-organic groups and/or halide groups, particularly 3, 4, 5 or 6 functional groups. Examples of initiator cores are cyclic initiator core saccharides, i.e., cyclic saccharides, that are used as the initiator core and cyclic aliphatic compounds. Representatives of cyclic initiator core saccharides are cyclic monosaccharides in all stereoisomeric and enantiomeric forms, e.g., cyclic pentoses and hexoses, such as α- and β-D-glucose and derivatives thereof. Representative cyclic aliphatic compounds include cycloalkanes, such as trihydroxycycloalkanes, e.g., 1,3,5-trihydroxycycloalkanes, preferably 1,3,5-trihydroxycyclohexane, inositols, more preferably myo-inositol, as well as derivatives thereof.

BRIEF DESCRIPTION OF THE DRAWINGS

FIG. 2 also shows synthesis of dendrimers of higher generations, i.e., of dendrimers 11 and 12, FIG. 3 also shows the synthesis of dendrimers of higher generations, i.e., of dendrimers 17 and 18, FIG. 4 also shows the synthesis of dendrimers of higher generations, i.e., of dendrimers 23 and 24.

DETAILED DESCRIPTION OF THE INVENTION

Figure 1:
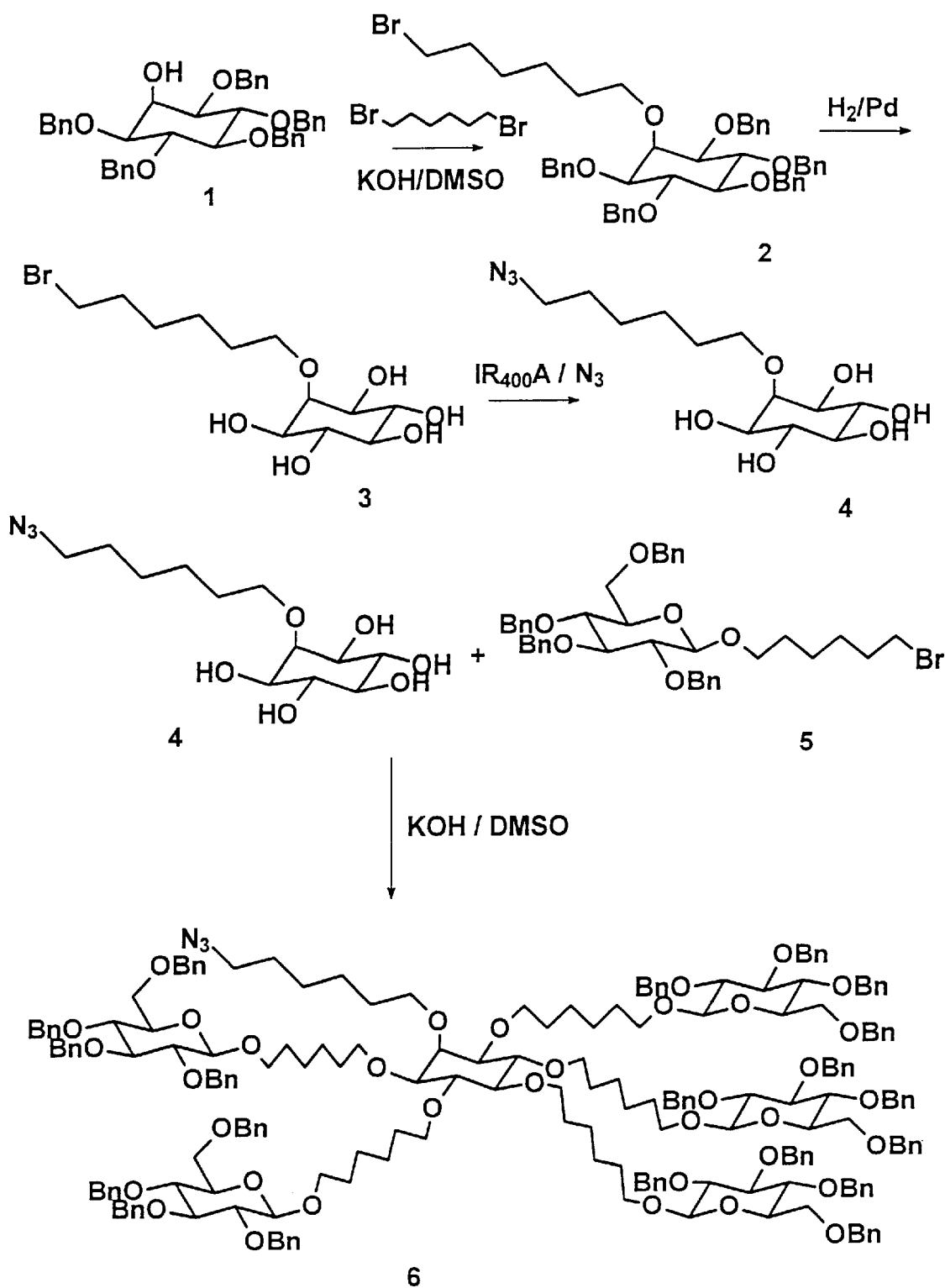
FIG. 1 shows the dendrimer 6 according to the invention comprising myo-inositol as the initiator core, β-D-glucose as the saccharide, a spacer, and an organic compound comprising 6 C atoms and having an azido group as a functional group.

A dendrimer according to the present invention has at least two saccharides that are bound to the initiator core. The term "saccharide" encompasses saccharides of any kind, particularly monosaccharides in all stereoisomeric and enantiomeric forms, e.g., pentoses and hexoses, such as α- and β-D-glucose and derivatives thereof, such as saccharides protected with protecting groups, e.g., benzyl, and/or saccharides modified with functional groups such as amino groups, phosphate groups or halide groups. Preferred saccharides include inositols, more preferably optically active derivatives of myo-inositol and quebrachitol, e.g., from galactinols, from both vegetable sources, such as sugar beets, and milk products, or derivatives obtained by enzymatic enantiomer separation. A dendrimer preferably has 3, 4, 5 or 6 saccharides. The saccharides may be the same or differ from one another. Moreover, the saccharides may be bound to the initiator core via a glycosidic bond.

In a preferred embodiment of a dendrimer according to the invention a spacer is present between the initiator core and one to maximally all saccharides. Examples thereof include aliphatic compounds, such as alkanes. The spacer may also be an unsaturated aliphatic compound. The spacer preferably has 3 to 10 C atoms. In addition, the spacer can be bound to the functional groups of the initiator core and/or the saccharides. If several spacers are present, they may be the same or different.

A dendrimer according to the present invention preferably comprises an organic compound. It may be bound to the initiator core and/or to one or several saccharides. Examples of organic compounds include alkanes having a functional group, e.g., a halogen, such as bromine, a hydroxy, azido and/or amino group, or alkenes, particularly with a terminal double bond. The alkenes may also have the above functional groups. The above organic compound preferably has 3 to 10 C atoms. In addition, one or more organic compounds may be present in a dendrimer according to the invention. If several organic compounds are present, they may be the same or different. By means of the organic compounds, it is possible to bind the dendrimer to a carrier and/or to attach dyes or colorants, magnetic particles and/or other components to the dendrimer.

Preferred first-generation dendrimers are compounds 6, 10, 16, 21, 22 and 28 represented in FIGS. 1 to 5.

First-generation dendrimers may also be synthesized into dendrimers of the second and higher generations by using the above initiator cores, saccharides, optionally spacers and/or organic compounds. Such dendrimers are also contemplated within the scope of the present invention.

For example, a second-generation dendrimer may be one in which further saccharides are bound to one or more saccharides of a first-generation dendrimer. Another second-generation dendrimer may be, e.g., one that includes at the saccharide of a first-generation dendrimer another initiator core to which further saccharides are bound. A second-generation dendrimer is also one in which two or more initiator cores of a first-generation dendrimer are linked with one another via another initiator core. In the above dendrimers of the second and optionally higher generations, the above spacers may be present between the initiator cores and the saccharides. Also, the above organic compounds may be bound thereto.

Figure 2:
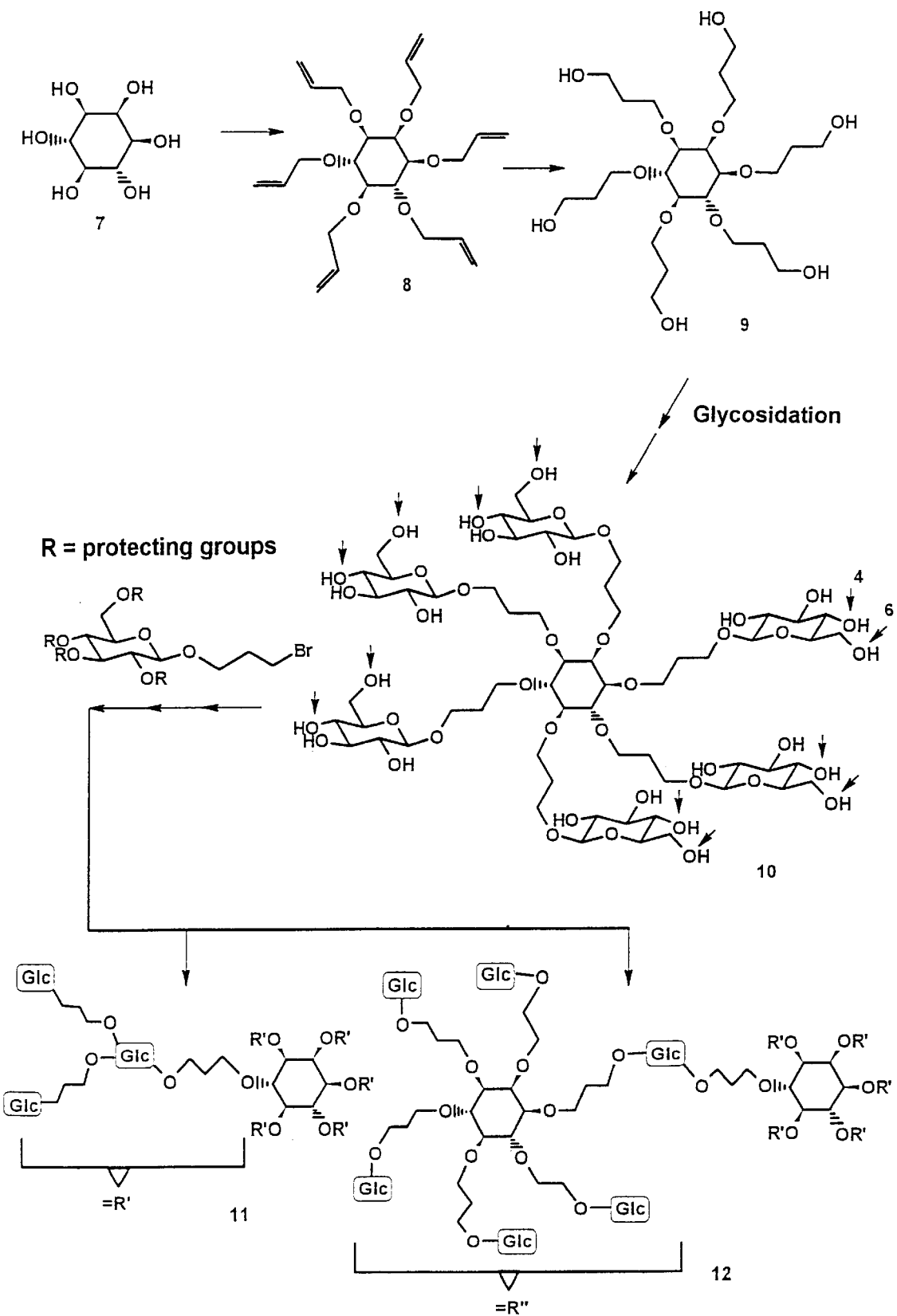
FIG. 2 shows the dendrimer 10 according to the invention comprising myo-inositol as the initiator core, β-D-glucose as the saccharide, and a spacer.
Figure 3:
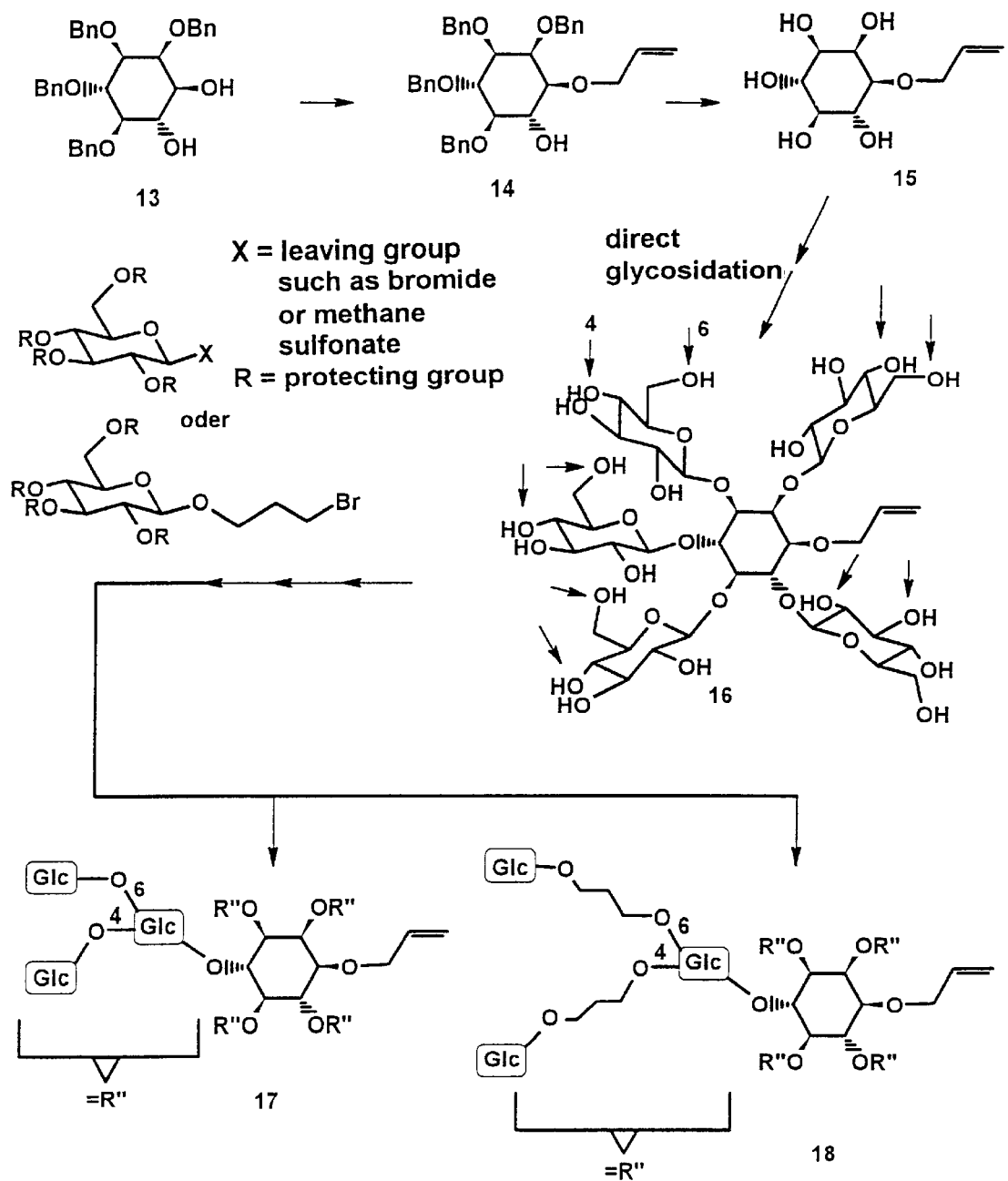
FIG. 3 shows the dendrimer 16 according to the invention comprising myo-inositol as the initiator core, β-D-glucose as the saccharide and an allyl residue as the organic compound.
Figure 4:
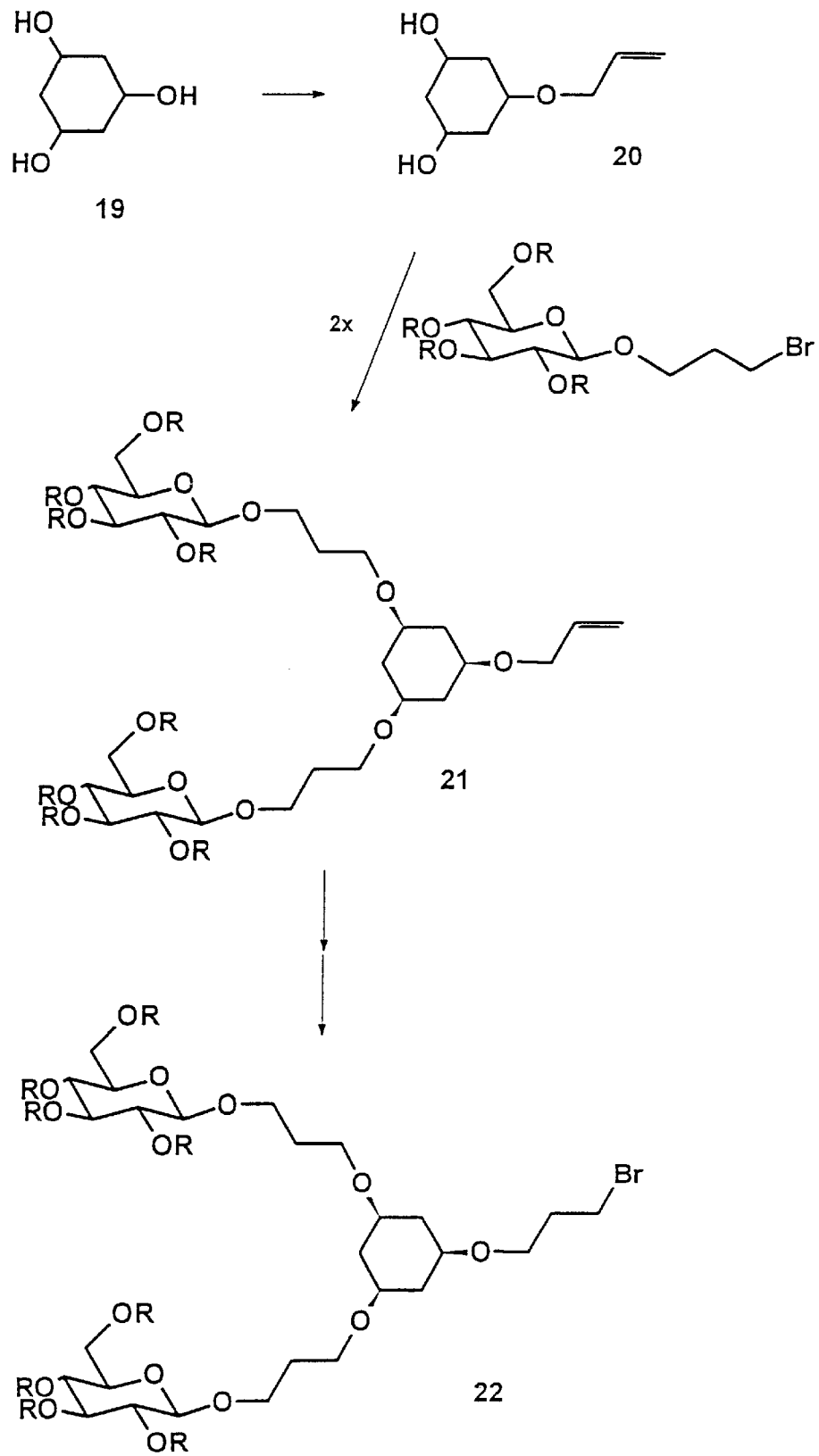
FIG. 4 shows the preparation of dendrimers 21 and 22 according to the invention, comprising 1,3,5-trihydroxycyclohexane as the initiator core, β-D-glucose as the saccharide, a spacer and an organic compound.
Figure 4:
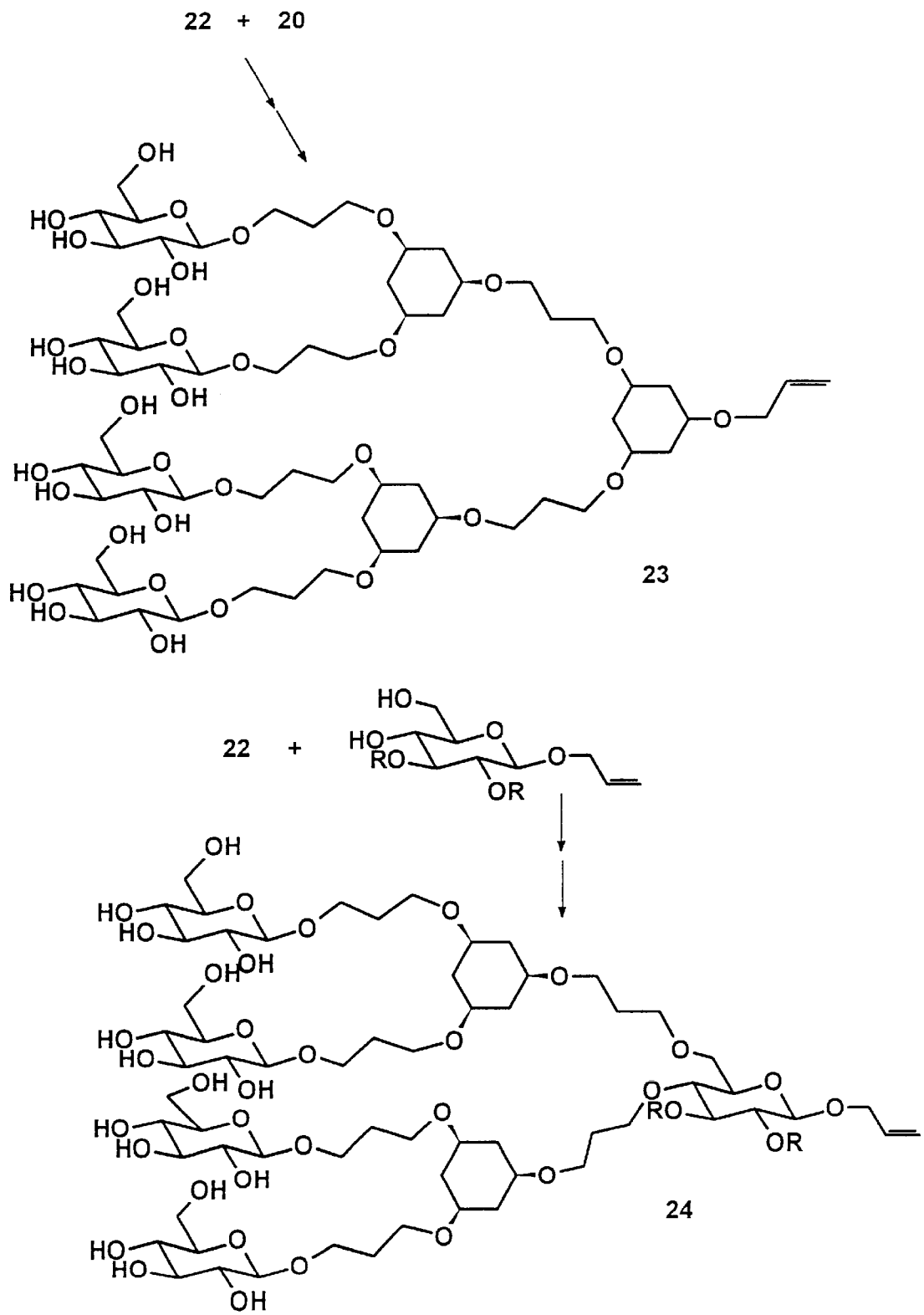

Examples of second-generation dendrimers include compounds 11, 12, 17, 18, 23 and 24 represented in FIGS. 2 to 4.

The components of dendrimers according to the present invention are shown as educts. However, they may be present in derivatized form in the dendrimers.

A process for the preparation of dendrimers is also provided according to the present invention. In this process, the individual components, i.e., initiator cores, saccharides, optionally linkers and optionally organic compounds, are bonded covalently with one another. This is done as usual. In this connection, reference is made to the preparation of the dendrimers in FIGS. 1 to 4 by way of example.

Dendrimers according to the present invention distinguish themselves by a number of favorable properties. They are biodegradable. Therefore, they can easily be disposed. In addition, they are made substantially from renewable raw materials. This saves fossil raw materials and the $CO_2$ balance is kept neutral. Moreover, dendrimers according to the present invention are present in accurately defined structures, i.e., there are no defects and/or intermolecular or intramolecular bonds. In addition, dendrimers according to the present invention have chiral C atoms. Further, they can bind chemical compounds well because of their structure and easily release them again under suitable conditions. In addition, dendrimers according to the present invention are capable of entering into selective interactions with sugar-specific receptors thus binding to viruses, bacteria and cells.

As a result, dendrimers according to the present invention are perfectly suited as column material for the separation of substances from mixtures of products, particularly for the separation of racemates in enantiomers. Also, because of their interactions with receptors, they can be used for the affinity-chromatographic isolation of lectins and other glycoproteins as well as cell-adhesion inhibitors, e.g., of viruses and bacteria for protection from infection.

Moreover, dendrimers according to the present invention can be provided for other applications. For example, they can be used as catalysts for enantioselective synthesis. They may also be used in the medical field, e.g., as excipients or drug carriers, particularly for use in sustained-release drugs and for the well-calculated introduction of active substances into target cells (drug-targeting). In addition, they can be used for preventing rejection reactions in the case of organ transplants. Dendrimers according to the present invention can also be used for the surface coating of aqueous media and as micelles particularly when they carry functional groups, such as amino groups, on their outermost shell, they can be used for transfection as multi-antigenic determinants, artificial vaccines or enzyme models in analogy with cyclodextrins. Also, dendrimers according to the present invention, which are solid phase-conjugated, particularly derivatives of inositol, can be used for preparing drinking water contaminated with bacteria. When linked with dyes or colorants, dendrimers according to the invention can be used for labeling lectins in histochemical and cytochemical processes.

The following examples explain the invention. However, they are purely exemplary and should not be taken as limiting.

EXAMPLE 1

Preparation of Dendrimer 6 According to the Invention

The preparation of dendrimer 6 and its structure are shown in FIG. 1.

a) Preparation of 2-O-(6-bromo-hexyl)-1,3,4,5,6-penta-O-benzyl-myo-inositol 2

5 g (7.9 mmoles) of 1,3,4,5,6-penta-O-benzyl-myo-inositol 1 were stirred in 60 ml absolute DMSO in the absence of moisture at room temperature. 1.8 g (4 times the excess) of potassium hydroxide powder were admixed and homogenized in the ultrasonic bath. After 10 minutes, 10 ml (8.26 times the excess) of 1,6-dibromohexane were admixed with stirring. The batch was poured onto ice-cold $NaHCO_3$, solution after 1 hour and first extracted with diethyl ether and then with petroleum ether. The combined organic phases were subsequently extracted by shaking several times with water, dried with $Na_2SO_4$, and separated on a silica gel column, eluent: PE/EE 8:1 (v/v). 2 was obtained as colorless oil (yield 5.8 g), which fully crystallized.

b) Preparation of 2-O-(6-bromo-hexyl)-myo-inositol 3

5 g (6.3 mmoles) of 2 were stirred with 0.5 g 20% Pd/C catalyst in 150 ml methanol/acetone 1:1 (v/v) in a $H_2$ atmosphere. After 3 hours, the catalyst was filtered off, and the solution was concentrated. 3 was obtained as colorless flakes (yield 2.2 g).

c) Preparation of 2-O-(6-azido-hexyl)-myo-inositol 4

1 g (2.9 mmoles) of 3 were stirred with 5 g amberlite IR 400 A ion exchanger (azido form) in 100 ml methanol. The ion exchanger was converted from the chloride form into the azido form by stirring (10 minutes) with a 20% $NaN_3$ solution and subsequent washing first with methanol, then with acetone and finally with diethyl ether and subsequent drying. After 12 hours, the ion exchanger was filtered off and the solution was concentrated. 4 was obtained as colorless flakes (yield 800 mg).

d) Preparation of 1,3,4,5,6-(6,2,3,4,6-tetra-O-benzyl-β-D-glucosyl-hexyl-2-O-(6-azido-hexyl)-myo-inositol 6

20 mg (0.065 mmole) of 4 were stirred in 2 ml absolute DMSO at room temperature with 20 mg (1 times the excess) of potassium hydroxide powder. After 5 minutes, 230 mg of 6-bromo-hexyl-2,3,4,6-tetra-O-benzyl-β-D-glucoside 5 (5* 1 times the excess) were added. Another 20 mg potassium hydroxide powder and 230 mg 5 were added after 2 and 5 hours. After a total of 10 hours, the batch was poured onto ice water and extracted with acetic ethyl ester. After drying with $Na_2SO_4$, the resultant dendrimer 6 was isolated by column chromatography on silica gel, eluent: PE/EE 1:1 (v/v).

The benzyl groups can be cleaved from the resultant dendrimer 6 according to the invention as usual.

EXAMPLE 2

Separation of a Racemate by Means of Dendrimer 6 According to the Invention

Dendrimer 6 according to the invention was filled into a common glass column and equilibrated with ethanol. Then, a racemate which comprises both enantiomers of thalidomide was applied onto the column. Elution was carried out with ethanol. Two products were obtained. By determining the value of rotation as usual, the products were each identified as the two enantiomers of thalidomide. This example shows that the dendrimers according to the invention are perfectly suited as column material for separating racemates.

EXAMPLE 3

Preparation of Dendrimer 28 According to the Invention

Figure 5:
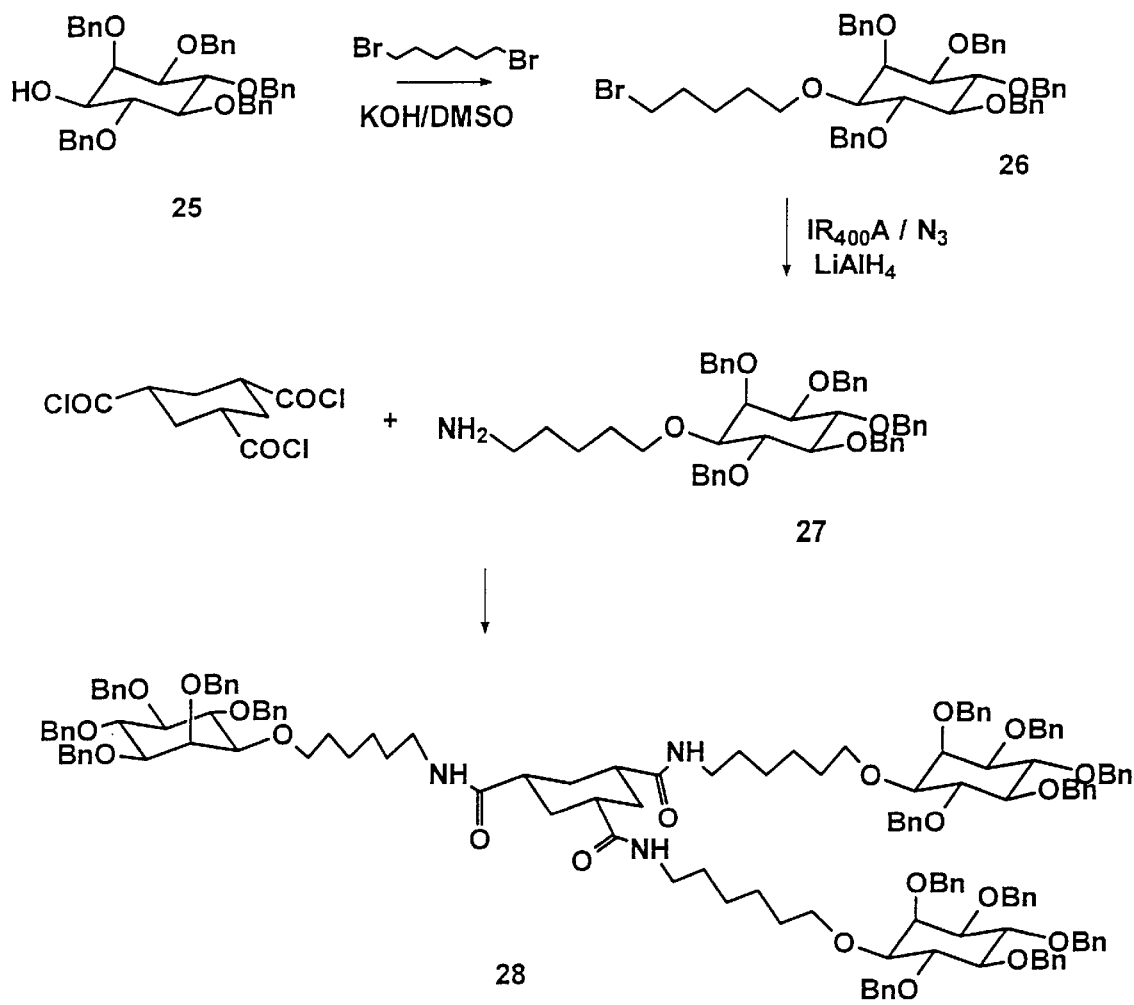
FIG. 5 shows the preparation of dendrimer 28 according to the invention.

The preparation of dendrimer 28 and its structure are shown in FIG. 5.

a) Preparation of L(−)-1-O-(6-bromo-hexyl)-2,3,4,5,6-penta-O-benzyl-myo-inositol 26.

250 mg (0.4 mmole) of L(−)-2,3,4,5,6-penta-O-benzyl-myo-inositol 25 (prepared from galactinol according to the method by Ballou et al., *J. Am. Chem. Soc.*, 82:3333 (1960)) were added by stirring into 5 ml absolute DMSO in the absence of moisture at room temperature. The mixture was admixed with 200 mg (4 times) potassium hydroxide powder and homogenized in the ultrasonic bath. After 10 min, 500 µl 1,6-dibromohexane were added by stirring. After 1 hour, the mixture was poured onto ice-cold $NaHCO_3$, solution and extracted three times with 10 ml diethyl ether. The combined organic extracts were shaken out several times with water, dried with $Na_2SO_4$, and separated on a silica gel column, eluent: PE/EE 8:1 (v/v).

b) Preparation of L(−)-1-O-(6-amino-hexyl)-2,3,4,5,6-penta-O-benzyl-myo-inositol 27.

3 g (3.78 mmoles) of L(−)-1-O-(6-bromo-hexyl)-2,3,4,5,6-penta-O-benzyl-myo-inositol 26 were stirred with 5 g amberlite IR 400 A ion exchanger (azido form) in 50 ml absolute acetone. The ion exchanger was converted from the chloride form into the azido form by stirring (10 min.) with a 20% $NaN_3$ solution, and subsequent washing with methanol→acetone→diethyl ether, then drying. After 12 h, the ion exchanger was filtered off, and the solution was concentrated. It was taken up with 15 ml diethyl ether/15 ml triethylamine and admixed with 500 mg lithium aluminum hydride. The reaction mixture was refluxed for 2 h. Then, it was mixed with 50 ml water and 25 ml diethyl ether, and the organic phase was separated. The aqueous phase was extracted twice with 20 ml diethyl ether. The combined organic extracts were shaken out several times with water, dried with $Na_2SO_4$ and separated on a silica gel column, eluent: PE/EE 10:1 (v/v).

c) Preparation of L(−)-tris-cis-cis-cyclohexane-1,3,5-carboxylic acid (1-O 6-aminohexyl (-2,3,4,5,6-penta-O-benzyl)-myo-inositol)-amide 28 To a solution of 270 mg (1 mmole) cis-cis-cyclohexane-1,3,5-carboxylic acid chloride, cooled down to −10° C., and 1 ml absolute pyridine in 10 ml absolute dichloromethane, there was added dropwise by stirring a solution of 2.2 g (3 mmoles) L(−)-1-O-(6-amino-hexyl)-2,3,4,5,6-penta-O-benzyl-myo-inositol 27 in further 10 ml absolute dichloromethane for 10 min. The mixture was slowly raised to room temperature for 1 h and stirred for another 2 h. Then, it was poured onto ice-cold $NaHCO_3$ solution and extracted with acetic ethyl ester. The combined organic extracts were shaken out several times with water, and the product was isolated after drying with $NA_2SO_4$ by column chromatography on silica gel, eluent: PE/EE 1:1 (v/v).

What is claimed is:

1. A dendrimer comprising: (a) an initiator core having at least two functional groups, (b) at least two saccharides, and (c) spacers between the initiator core and the saccharides, wherein the initiator core comprises a cyclic initiator core saccharide or a cyclic aliphatic compound, the functional groups are selected from the group consisting of hydroxy groups, hydroxyalkyl groups, amino groups, carboxylic acid groups and halide groups, the spacer is an aliphatic residue of 3 to 10 carbon atoms, and the spacers are attached to the initiator core through the functional groups.

2. The dendrimer according to claim 1, wherein the cyclic initiator core saccharide is a cyclic monosaccharide or a derivative thereof.

3. The dendrimer according to claim 2, wherein the cyclic monosaccharide is β-D-glucose.

4. The dendrimer according to claim 1, wherein the cyclic aliphatic compound is a $C_6$ cycloalkane.

5. The dendrimer according to claim 4, wherein the $C_6$ cycloalkane is selected from the group consisting of a trihydroxycyclohexane, inositol, or a derivative thereof.

6. The dendrimer according to claim 1, wherein the saccharides of (b) are selected from the group consisting of a monosaccharide and inositol or a derivative thereof.

7. The dendrimer according to claim 6, wherein the monosaccharide is glucose.

8. The dendrimer according to claim 1, wherein the dendrimer has 3, 4, 5 or 6 saccharides of (b).

9. The dendrimer according to claim 1, wherein the saccharides of (b) are the same.

10. The dendrimer according to claim 1, wherein the aliphatic residue is a saturated or unsaturated aliphatic compound.

11. The dendrimer according to claim 1, wherein the dendrimer further comprises an organic compound bound to the initiator core or to one or more saccharides of (b).

12. The dendrimer according to claim 11, wherein the organic compound is an alkane having a functional group or is an alkene.

13. The dendrimer according to claims 12, wherein the functional group is selected from the group consisting of a halogen, a hydroxy, an azido and an amino group.

14. The dendrimer according to claim 11, wherein the organic compound has 3 to 10 C atoms.

15. The dendrimer according to claim 1, wherein the dendrimer comprises more than one organic compound bound to the initiator core, or to one or more saccharides of (b).

16. The dendrimer according to claim 1, wherein the dendrimer is of the second or higher generation.

17. A dendrimer of compound 23 or compound 24, wherein R is a protecting group molecule having at least two functional groups.

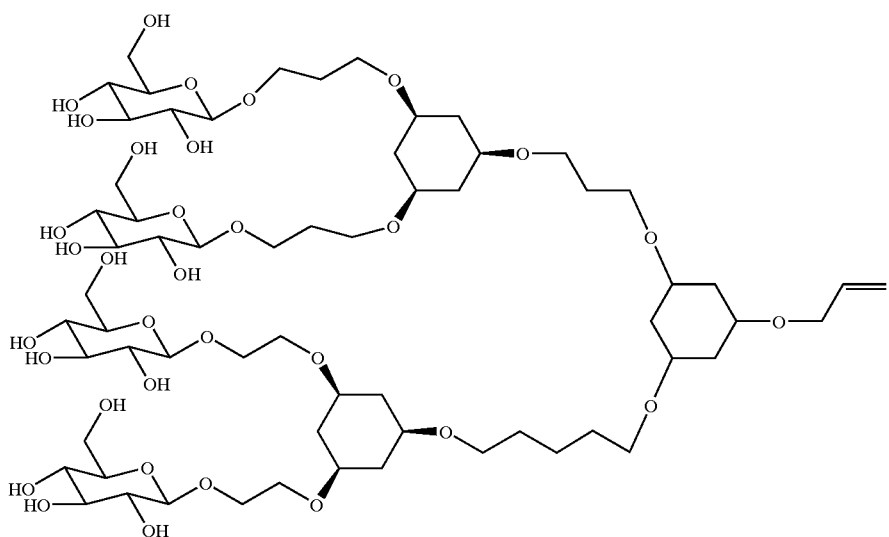

23

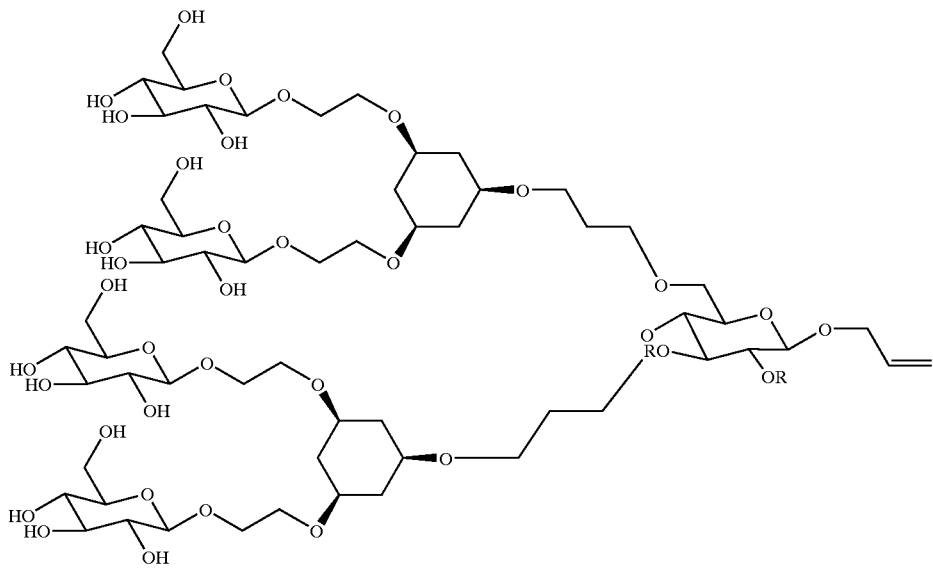

24

18. A process for of preparing a dendrimer according to claim 1 comprising the steps of:
  (a) reacting an initiator core molecule having at least two functional groups with an aliphatic compound having 3 to 10 carbon atoms,
  (b) purifying the obtained product of (a),
  (c) reacting the purified product of (b) with an activated saccharide having protecting groups,
  (d) purifying the obtained product of (c), and
  (e) removing the protecting groups.

19. The process according to claim 18, further comprising the step of reacting the obtained product of (e) with an organic compound.

* * * * *